US010113135B2

(12) United States Patent
Tanaka et al.

(10) Patent No.: US 10,113,135 B2
(45) Date of Patent: Oct. 30, 2018

(54) PERFUMING METHOD

(71) Applicant: KAO CORPORATION, Tokyo (JP)

(72) Inventors: Sakuya Tanaka, Wakayama (JP);
Sachiko Nihei, Funabashi (JP);
Yasutomo Arai, Wakayama (JP)

(73) Assignee: KAO CORPORATION, Tokyo (JP)

( * ) Notice: Subject to any disclaimer, the term of this patent is extended or adjusted under 35 U.S.C. 154(b) by 73 days.

(21) Appl. No.: 15/105,271

(22) PCT Filed: Dec. 18, 2014

(86) PCT No.: PCT/JP2014/083582
§ 371 (c)(1),
(2) Date: Jun. 16, 2016

(87) PCT Pub. No.: WO2015/093572
PCT Pub. Date: Jun. 25, 2015

(65) Prior Publication Data
US 2016/0312150 A1   Oct. 27, 2016

(30) Foreign Application Priority Data
Dec. 19, 2013  (JP) ................................ 2013-263088

(51) Int. Cl.
C11B 9/00       (2006.01)
A61K 8/37       (2006.01)
A61Q 13/00      (2006.01)
C07C 69/24      (2006.01)
C07C 69/44      (2006.01)
C07C 69/50      (2006.01)
C07C 69/58      (2006.01)
C11D 3/50       (2006.01)
A61K 8/49       (2006.01)
A61Q 5/02       (2006.01)
A61Q 5/06       (2006.01)
A61Q 5/12       (2006.01)
A61Q 19/00      (2006.01)
A61Q 5/00       (2006.01)
A61Q 19/10      (2006.01)

(52) U.S. Cl.
CPC ............ C11B 9/0061 (2013.01); A61K 8/37 (2013.01); A61K 8/498 (2013.01); A61Q 5/02 (2013.01); A61Q 5/06 (2013.01); A61Q 5/12 (2013.01); A61Q 13/00 (2013.01); A61Q 19/007 (2013.01); C07C 69/24 (2013.01); C07C 69/44 (2013.01); C07C 69/50 (2013.01); C07C 69/58 (2013.01); C11B 9/003 (2013.01); C11B 9/008 (2013.01); C11D 3/507 (2013.01); A61Q 5/00 (2013.01); A61Q 19/00 (2013.01); A61Q 19/10 (2013.01)

(58) Field of Classification Search
CPC .................................................. C11B 9/0061
See application file for complete search history.

(56) References Cited

U.S. PATENT DOCUMENTS

| 5,137,036 A | 8/1992 | Southwick |
| 5,562,847 A | 10/1996 | Waite et al. |
| 5,649,979 A | 7/1997 | Paget et al. |
| 5,726,345 A | 3/1998 | Paget et al. |
| 2003/0125220 A1 | 7/2003 | Dykstra et al. |
| 2004/0220074 A1 | 11/2004 | Fehr et al. |
| 2005/0014663 A1 | 1/2005 | Dykstra et al. |
| 2005/0227879 A1 | 10/2005 | Dykstra et al. |
| 2009/0047223 A1 | 2/2009 | Natsch et al. |
| 2009/0181878 A1 | 7/2009 | Fehr et al. |
| 2009/0203774 A1 | 8/2009 | Amino et al. |
| 2009/0312231 A1* | 12/2009 | Huchel ................. A61K 8/585 512/10 |
| 2010/0087524 A1 | 4/2010 | Haiber et al. |
| 2012/0082628 A1 | 4/2012 | Haught et al. |

FOREIGN PATENT DOCUMENTS

| JP | 8-502522 A | 3/1996 | |
| JP | 10265325 A | 10/1998 | |
| JP | 11-500485 A | 1/1999 | |
| JP | 2000-512663 A | 9/2000 | |
| JP | 2003-313580 A | 11/2003 | |
| JP | 2005-502768 A | 1/2005 | |
| JP | 2005-511710 A | 4/2005 | |
| JP | 2009-520701 A | 5/2009 | |
| WO | WO-9730687 A2 * | 8/1997 | .............. A61K 8/37 |
| WO | 2008/001912 A1 | 1/2008 | |

(Continued)

OTHER PUBLICATIONS

International Search Report dated Mar. 31, 2015 in PCT/JP2014/083582 filed Dec. 18, 2014.
Extended European Search Report dated May 24, 2017 in European Patent Application No. 14872188.9.
Dikusar—"New Esters of Vanillin and Vanillal with Some Alkane- and Arenecarboxylic Acids", Russian Journal of Applied Chemistry. 2006, vol. 79, No. 6, pp. 1035-1037.
Dikusar et al.—"2-[3-Alkoxy-4-(hydroxyl, alkoxy, acyloxy)phenyl]-2,3-dihydro-1H-benzimidazoles on the Basis of Vanillin and Vanillal Derivatives", Russian Journal of General Chemistry, 2007, vol. 77, No. 11, pp. 1924-1927.

(Continued)

Primary Examiner — Arrie L Reuther
(74) Attorney, Agent, or Firm — Oblon, McClelland, Maier & Neustadt, L.L.P.

(57) ABSTRACT

Provided is a perfuming method including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palimitic acid, stearic acid, oleic acid, adipic acid, and sebacic acid; and subsequently bringing the perfume precursor into contact with moisture in the air to perform hydrolysis, thereby releasing a perfume.

13 Claims, No Drawings

(56) References Cited

FOREIGN PATENT DOCUMENTS

WO    WO 2008/105652 A1    9/2008
WO       2012/044728 A1    4/2012

OTHER PUBLICATIONS

Dikusar et al.—"Synthesis of Schiff Bases from 1-Naphthylamine and Vanillin, Vanillal and Their O-Acyl Derivatives", Russian Journal of Organic Chemistry, 2006, vol. 42, No. 3, pp. 369-375.
Li et al.—"Thermotropic Liquid Crystalline Polymer. III. Synthesis and Properties of Poly(amide-Azomethine-Ester)". Journal of Polymer Science, Part A, 1991. vol. 29, No. 3, pp. 361-367.
Sanui et al.—"Active Polycondensation with Hexamethylenediamine of Sebacates having 1,4-Pyrone Nuclei" Journal of Polymer Science, Polymer Chemistry Edition, 1977, vol. 15, No. 5, pp. 1107-1115.

* cited by examiner

PERFUMING METHOD

FIELD OF THE INVENTION

The present invention relates to a perfuming method.

BACKGROUND OF THE INVENTION

In recent years, in view of an increase in awareness regarding fragrance of clothing, cosmetics, etc., various investigations of techniques on persistent perfumes have been made. As an example, there is proposed a technique for persistently generating a perfume by using an ester of a fragrant alcohol.

Specifically, PTL 1 (JP 8-502522A) discloses a process for perfuming textiles through a treatment with a detergent and/or a softener containing an ester compound of a specified fragrant alcohol and a carboxylic acid having a specified C7 to C24 alkyl group.

PTL 2 (JP 2000-512663A) discloses a fragrance precursor composition containing an ester of an odoriferous alcohol and an acid having an optionally substituted C1-C30 alkyl group or the like.

In addition, PTL 3 (JP 2003-313580A) discloses a sustained release perfume composition using a mixture of a dibasic acid monoester and/or a dibasic acid diester, and ethylene glycol or propylene glycol, or the like for the purpose of retaining a fragrance for a long period of time.

Furthermore, PTL 4 (JP 2009-520701A) discloses a malodor counteracting preparation for oral use containing a specified esterified fumarate for the purpose of preventing or reducing an oral malodor.

SUMMARY OF THE INVENTION

The present invention relates to a perfuming method including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact with moisture in the air to perform hydrolysis, thereby releasing a perfume.

DETAILED DESCRIPTION OF THE INVENTION

Ester compounds derived from a fragrant alcohol have properties for gradually releasing a fragrant alcohol (sustained release properties) through hydrolysis, and hence, they are useful as a perfume precursor. However, perfume-derived ester compounds having a phenol structure or a hydroxypyrone structure are poor in storage stability and particularly instable in a water-based product, so that it was difficult to regulate the sustained release properties of a perfume. In addition, for example, when a stable molecular structure is taken in order to improve the storage stability in water, it is difficult to control the release of a perfume, and a special treatment utilizing an enzyme or a microorganism becomes needed. Even in PTLs 1 to 4, thorough investigations are not made on simple and easy control of the sustained release properties of such a perfume-derived ester compound.

The present invention is concerned with a perfume composition excellent in storage stability, particularly stability in a water-based product and capable of sustainedly releasing a perfume over a long period of time, a perfuming method using the same, and a fabric treating agent, a softener, a cosmetic, a hair cosmetic, and a detergent each containing this perfume composition and use for perfuming.

The present inventors have found that by using an ester of a perfume having a phenol structure or a hydroxy-4-pyrone structure and a carboxylic acid having a specified hydrocarbon moiety, a perfume precursor excellent in storage stability, particularly stability in a water-based product and capable of sustainedly releasing a perfume over a long period of time is obtained.

That is, the present invention is concerned with the following [1] to [8] aspects.

A perfuming method including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact with moisture in the air to perform hydrolysis, thereby releasing a perfume.

A perfume composition containing a perfume precursor composed of an ester of a perfume having a phenol structure or a hydroxy-4-pyrone structure and an aliphatic monocarboxylic acid having 8 or more and 18 or less carbon atoms or an aliphatic dicarboxylic acid having 6 or more and 20 or less carbon atoms.

A fabric treating agent containing the perfume composition.

A softener containing the perfume composition.

A cosmetic containing the perfume composition.

A hair cosmetic containing the perfume composition.

A detergent containing the perfume composition.

Use for perfuming including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact moisture in the air to perform hydrolysis, thereby releasing a perfume.

In accordance with the present invention, it is possible to provide a perfume composition excellent in storage stability particularly stability in a water-based product and capable of sustainedly releasing a perfume over a long period of time; a perfuming method using the same; a fabric treating agent, a softener, a cosmetic, a hair cosmetic, and a detergent each containing this perfume composition; and use for perfuming.

The perfuming method of the present invention is a perfuming method including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact with moisture in the air to perform hydrolysis, thereby releasing a perfume.

Upon explaining the perfuming method of the present invention, the perfume precursor and the like related to the perfuming method of the present invention are first explained.

[Perfume Precursor]

The perfume precursor which is used for the perfume composition of the present invention is composed of an ester of a perfume having a phenol structure or a hydroxy-4-pyrone structure and an aliphatic monocarboxylic acid having 8 or more and 18 or less carbon atoms or an aliphatic dicarboxylic acid having 6 or more and 20 or less carbon atoms.

Though the reasons why the perfume precursor is excellent in storage stability, particularly stability in a water-based product and is capable of sustainedly releasing a perfume over a long period of time are not always elucidated yet, the following may be considered.

The perfume precursor is an ester of a perfume having a phenol structure or a hydroxy-4-pyrone structure and an aliphatic monocarboxylic acid or an aliphatic dicarboxylic acid having a relatively long-chain hydrocarbon moiety, and its molecular structure is hydrophobic and has a cyclic structure derived from the perfume and a chain structure derived from the aliphatic monocarboxylic acid or aliphatic dicarboxylic acid. According to this, it may be considered that in water of the water-based product or the like, the ester molecules are liable to come close to each other, and the action of the water molecule on the ester group moiety is hindered by the hydrophobic group, so that the perfume precursor is hardly hydrolyzed.

In addition, in the case where an oil or a surfactant is present in the water-based product, in view of the fact that the hydrophobic moiety of the oil or surfactant in the water-based product and the long-chain hydrocarbon moiety derived from the aliphatic monocarboxylic acid or the like have an high affinity with each other, the oil or surfactant takes the surroundings of the ester molecules therein, and the ester bonding moieties more hardly come into contact with water, so that the hydrolysis is hardly advanced, and hence, it may be considered that the perfume precursor becomes more excellent in stability in the water-based product.

Such stability in water is caused due to the fact that the perfume precursor ester has the aforementioned cyclic structure and the aforementioned chain structure in an appropriate balance, and it may be considered that when maltol, ethyl maltol, vanillin, ethyl vanillin, or raspberry ketone having a phenol structure or a hydroxy-4-pyrone structure is combined as the perfume with an aliphatic monocarboxylic acid having 8 or more and 18 or less carbon atoms or an aliphatic dicarboxylic acid having 6 or more and 20 or less carbon atoms, an especially conspicuous effect is brought.

Meanwhile, by applying the perfume precursor to a fabric or a human body to bring the perfume precursor itself into contact with the air, the perfume precursor is present in a dispersed state where a distance between the respective molecules becomes large in view of the fact that the action of the hydrophobic moiety between the molecules becomes loose. Thus, it may be considered that the ester moiety derived from the phenol structure or hydroxy-4-pyrone structure having a hydroxyl group with a relatively high acidity becomes in a state where it is liable to be relatively hydrolyzed with moisture in the air, so that a strong fragrance is revealed over a long period of time.

<Perfume>

In the perfume precursor, as the perfume, a perfume having a phenol structure or a hydroxy-4-pyrone structure is used.

The "perfume" as referred to in the present invention means a substance that allows a smell to be sensed and refers to a "fragrance".

A pKa of the perfume having a phenol structure or a hydroxy-4-pyrone structure is preferably 13 or less, more preferably 7 or more and 12 or less, and still more preferably 7.5 or more and 11.5 or less. When the pKa falls within the foregoing range, a strong fragrance may be revealed over a long period of time.

The pKa as referred to in the present invention means an acid dissociation constant and is expressed by a negative common logarithm pKa of an equilibrium constant Ka in a dissociation reaction in which a hydrogen ion is released. It is meant that the smaller the pKa, the stronger the acid is. In calculating the pKa in the present invention, SPARC (SPARC Performs Automated Reasoning in Chemistry, ARChem, LP, http://www.archemcalc.com/sparc.html) that is a chemical structure-physical property calculation site which is constructed on the internet was used.

As for the perfume having a phenol structure, the carbon number is preferably 7 or more, more preferably 8 or more, and still more preferably 9 or more; and preferably 14 or less, more preferably 10 or less, still more preferably 9 or less, and yet still more preferably 9. When the carbon number falls within the foregoing range, the perfume may be sustainedly released over a long period of time.

Specifically; there are exemplified vanillin (carbon number: 8, pKa: 7.8), ethyl vanillin (carbon number: 9, pKa: 7.8), isoeugenol (carbon number: 10, pKa: 9.8), benzyl salicylate (carbon number: 14, pKa: 9.8), cis-3-hexenyl salicylate (carbon number: 13, pKa: 9.8), vanillin PGA (carbon number: 11, pKa: 9.8), cyclohexyl salicylate (carbon number: 13, pKa: 10.0), eugenol (carbon number: 10, pKa: 10.0), zingerone (carbon number: 11, pKa: 10.0), vanitrope (carbon number: 11, pKa: 10.0), raspberry ketone (carbon number: 10, pKa: 10.1), methyl salicylate (carbon number 8, pKa: 10.1), hexyl salicylate (carbon number: 13, pKa: 10.1), carvacrol (carbon number: 10, pKa: 10.5), and thymol (carbon number: 10, pKa: 10.9).

As for the perfume having a hydroxy-4-pyrone structure, the carbon number is preferably 6 or more, and more preferably 7 or more; and preferably 10 or less, more preferably 7 or less, and still more preferably 7. When the carbon number falls within the foregoing range, the perfume may be sustainedly released over a long period of time.

Specifically, there may be exemplified maltol (carbon number: 6, pKa: 11.2) and ethyl maltol (carbon number: 7, pKa: 11.3).

Among the aforementioned perfumes, from the viewpoints of enabling the storage stability to be improved and improving the sustained release performance, maltol, ethyl maltol, vanillin, ethyl vanillin, and raspberry ketone are preferred.

These perfumes may be used solely or may be used in combination of two or more thereof.

In the perfume precursor, an aliphatic monocarboxylic acid having 8 or more and 18 or less carbon atoms or an aliphatic dicarboxylic acid having 6 or more and 20 or less carbon atoms is used as the aliphatic carboxylic acid.

<Aliphatic Monocarboxylic Acid>

As the aliphatic monocarboxylic acid, an aliphatic monocarboxylic acid having 8 or more and 18 or less carbon atoms is used.

By using an aliphatic monocarboxylic acid, the carbon number of which falls within the foregoing range, the affinity of the oil or surfactant in a water-based product with the hydrocarbon moiety of the ester is improved, and hence, the ester bonding moieties more hardly come into contact with water, the hydrolysis is hardly advanced, and the storage stability in the water-based product is improved.

From the viewpoint of improving the storage stability in the water-based product, the carbon number of the aliphatic monocarboxylic acid is 8 or more, preferably 10 or more, more preferably 11 or more, and still more preferably 12 or more; and from the viewpoints of atom efficiency of the perfume to be consumed and initial aromatization, the carbon number of the aliphatic monocarboxylic acid is 18 or less, preferably 16 or less, more preferably 14 or less, still more preferably 12 or less, and yet still more preferably 12.

Specific examples of the aliphatic monocarboxylic acid include aliphatic monocarboxylic acids, such as enanthic acid, caprylic acid, pelargonic acid, capric acid, undecylic acid, lauric acid, tridecylic acid, myristic acid, pentadecylic acid, palmitic acid, margaric acid, stearic acid, dimethyloctanoic acid, octenoic acid, decenoic acid, dodecenoic acid, tetradecenoic acid, hexadecenoic acid, oleic acid, vaccenic acid, linoleic acid, linolenic acid, etc.

In the present invention, from the viewpoints of atom efficiency of the perfume to be consumed and initial aromatization, among those, lauric acid, myristic acid, palmitic acid, stearic acid, and oleic acid are preferred, and lauric acid, stearic acid, and oleic acid are more preferred.

<Aliphatic Dicarboxylic Acid>

As the aliphatic dicarboxylic acid, an aliphatic dicarboxylic acid having 6 or more and 20 or less carbon atoms is used.

By using an aliphatic dicarboxylic acid, the carbon number of which falls within the foregoing range, the affinity of the oil or surfactant in a water-based product with the hydrocarbon moiety of the ester is improved, and hence, the ester bonding moieties more hardly come into contact with water, the hydrolysis is hardly advanced, and the storage stability in the water-based product is improved.

From the viewpoint of improving the storage stability in the water-based product, the carbon number of the aliphatic dicarboxylic acid is 6 or more, preferably 8 or more, more preferably 9 or more, and still more preferably 10 or more; and from the viewpoints of atom efficiency of the perfume to be consumed and initial aromatization, the carbon number of the liphatic dicarboxylic acid is 20 or less, preferably 16 or less, more preferably 14 or less, and still more preferably 12 or less.

Specific examples of the aliphatic dicarboxylic acid include aliphatic dicarboxylic acids, such as adipic acid, pimelic acid, suberic acid, azelaic acid, sebacic acid, dodecanedioic acid, tetradecanedioic acid, etc.

In the present invention, from the viewpoints of atom efficiency of the perfume to be consumed and initial aromatization, among those, adipic acid, suberic acid, azelaic acid, sebacic acid, and dodecanedioic acid are preferred, adipic acid and sebacic acid are more preferred, and sebacic acid is still more preferred.

[Production Method of Perfume Precursor]

The ester that constitutes the perfume precursor may be, for example, produced by the following (i) to (iv) methods.

(i) A method of esterifying directly the aforementioned perfume and the aforementioned aliphatic monocarboxylic acid or aliphatic dicarboxylic acid, thereby producing the perfume precursor.

(ii) A method of subjecting an ester obtained by allowing a lower alcohol, such as methanol, etc., and the aforementioned aliphatic monocarboxylic acid or aliphatic dicarboxylic acid to react with each other, to an ester interchange reaction with the aforementioned perfume, thereby producing the perfume precursor.

(iii) A method of allowing the aforementioned perfume and an acid halide of the aforementioned aliphatic monocarboxylic acid or aliphatic dicarboxylic acid to react with each other, thereby producing the perfume precursor.

(iv) A method of allowing the aforementioned perfume and an anhydride of the aforementioned aliphatic monocarboxylic acid or aliphatic dicarboxylic acid to react with each other, thereby producing the perfume precursor.

Among those methods, from the viewpoint of production efficiency, a method of allowing the aforementioned perfume and an acid halide of the aforementioned aliphatic monocarboxylic acid or aliphatic dicarboxylic acid to react with each other, thereby producing the perfume precursor is preferred.

More specifically, it is preferred to produce the perfume precursor by a method of subjecting a perfume having a phenol structure or a hydroxy-4-pyrone structure and an acid halide of an aliphatic monocarboxylic acid having 8 or more and 18 or less carbon atoms or an acid halide of an aliphatic dicarboxylic acid having 6 or more and 20 or less carbon atoms to a condensation reaction.

(Acid Halide)

The acid halide of the aliphatic monocarboxylic acid or the acid halide of the aliphatic dicarboxylic acid may be, for example, obtained through a reaction of the aliphatic monocarboxylic acid or aliphatic dicarboxylic acid with a halogenating reagent of every kind, such as thionyl chloride, phosphorus trichloride, phosphorus pentachloride, phosphorus tribromide, etc.

Among those, from the viewpoint of reactivity and the viewpoint of easiness of availability of the reagent, an acid halide obtained through a reaction of an aliphatic monocarboxylic acid or an aliphatic dicarboxylic acid with phosphorus trichloride is preferred, and especially, an acid chloride of an aliphatic monocarboxylic acid or an acid chloride of an aliphatic dicarboxylic acid is preferred.

(Blending Ratio)

From the viewpoint of not only allowing the reaction to proceed quickly but also reducing the amount of the unreacted aliphatic monocarboxylic acid, the charge amount of the perfume in performing the condensation reaction is preferably 0.9 moles or more, more preferably 0.95 moles or more, and still more preferably 0.98 moles or more per mole of the acid halide of an aliphatic monocarboxylic acid; and from the viewpoint of reducing the amount of the unreacted perfume, the charge amount of the perfume is preferably 1.1 moles or less, more preferably 1.05 moles or less, and still more preferably 1.02 moles or less per mole of the acid halide of an aliphatic monocarboxylic acid.

In addition, from the viewpoint of not only allowing the reaction to proceed quickly but also reducing the amount of the unreacted aliphatic dicarboxylic acid, the charge amount of the perfume in performing the condensation reaction is preferably 1.8 moles or more, more preferably 1.9 moles or more, and still more preferably 1.95 moles or more per mole of the acid halide of an aliphatic dicarboxylic acid; and from the viewpoint of reducing the amount of the unreacted perfume, the charge amount of the perfume is preferably 2.2 moles or less, more preferably 2.1 moles or less, and still more preferably 2.05 moles or less per mole of the acid halide of an aliphatic dicarboxylic acid.

(Solvent)

A solvent which is used for the condensation reaction is not particularly limited, and examples thereof include halogenated hydrocarbons such as chloroform and dichloromethane, aliphatic esters such as ethyl acetate and isopropyl acetate, aromatic hydrocarbons such as benzene, toluene, xylene, and ethylbenzene, alicyclic hydrocarbons such as cyclopentane, cyclohexane, methylcyclohexane, decalin, and tetralin, aliphatic hydrocarbons such as pentane, hexane, heptane, and octane, and the like.

Among those, from the viewpoint of dissolubility of the perfume and the aliphatic monocarboxylic acid or aliphatic dicarboxylic acid, ethyl acetate, dichloromethane, and toluene are preferred. These solvents may be used solely or may be used in combination of two or more thereof.

(Reaction Temperature)

From the viewpoint of performing the reaction without causing a loss of the raw materials, a reaction temperature of the condensation reaction is preferably a boiling point of each of the perfume and the aliphatic monocarboxylic acid or aliphatic dicarboxylic acid or lower. In addition, from the viewpoint of improving the reaction rate, a specific reaction temperature is preferably −20° C. or higher, more preferably −18° C. or higher, still more preferably −15° C. or higher, and yet still more preferably −12° C. or higher. From the viewpoint of controlling the reaction, the reaction temperature is preferably 80° C. or lower, and more preferably 65° C. or lower.

In the present invention, from the viewpoint of after performing the reaction at a temperature in the foregoing range, allowing the reaction to proceed thoroughly, it is preferred to perform agitation at a prescribed temperature for a prescribed time. A temperature in performing the agitation is preferably 10° C. or higher, more preferably 15° C. or higher, and still more preferably 20° C. or higher; and preferably 90° C. or lower, and more preferably 80° C. or lower.

The agitation is performed for preferably 0.5 hours or more, and more preferably 0.8 hours or more; and preferably 4 hours or less, more preferably 3 hours or less, still more preferably 2 hours or less, and yet still more preferably 1.5 hours or less.

(Reaction Pressure)

The condensation reaction may be performed at atmospheric pressure or under reduced pressure. From the viewpoint that the production may be performed with simple equipment, it is preferred to perform the production at atmospheric pressure.

A specific pressure in performing the condensation reaction is preferably 80 kPa or more, more preferably 90 kPa or more, and still more preferably 95 kPa or more; and preferably 101 kPa or less.

From the viewpoint of inhibiting a side reaction and the viewpoint of inhibiting incorporation of water into the reaction system, it is preferred to perform the condensation reaction in the presence of an inert gas. Examples of the inert gas include nitrogen, helium, argon, and the like. Among those, nitrogen is preferred from the viewpoint of performing the production while reducing costs.

(Basic Substance)

In the aforementioned production method, from the viewpoint of efficiently performing the condensation reaction, it is preferred to use a basic substance.

Examples of the basic substance may include triethylamine, tributylamine, pyridine, picoline, and diazabicycloundecene (DBU). Among those, from the viewpoint of easiness of availability and the viewpoint of handling properties, triethylamine is preferred.

The use amount of the basic substance is preferably 1 mole or more, more preferably 1.01 moles or more, still more preferably 1.02 moles or more, and yet still more preferably 1.04 moles or more per mole of the acid halide of an aliphatic monocarboxylic acid; and in view of balance between the use amount and the costs, the use amount of the basic substance is preferably 1.2 moles or less, more preferably 1.15 moles or less, still more preferably 1.1 moles or less, and yet still more preferably 1.06 moles or less per mole of the acid halide of an aliphatic monocarboxylic acid. In addition, the use amount of the basic substance is preferably 2 moles or more, more preferably 2.01 moles or more, still more preferably 2.02 moles or more, and yet still more preferably 2.04 moles or more per mole of the acid halide of an aliphatic dicarboxylic acid; and in view of balance between the use amount and the costs, the use amount of the basic substance is preferably 2.4 moles or less, more preferably 2.3 moles or less, still more preferably 2.2 moles or less, and yet still more preferably 2.15 moles or less per mole of the acid halide of an aliphatic dicarboxylic acid.

[Perfume Composition]

The perfume composition of the present invention is a composition which contains the aforementioned perfume precursor and which sustainedly releases the perfume having a phenol structure or a hydroxy-4-pyrone structure through hydrolysis.

The perfume composition of the present invention may further contain, in addition to the perfume precursor, other perfume, an oil, a surfactant, and an organic solvent.

The perfume composition of the present invention may be blended in various products and may sustainedly release a perfume having a phenol structure or a hydroxy-4-pyrane structure stably over a relatively long period of time, and hence, a fragrance derived from the perfume may be generated.

Examples of the product which the perfume composition of the present invention may be blended therein include nonaqueous solution-based products, such as an oil-based deodorant composition, a powder detergent, a solid soap, a bath additive, a sanitary material such as a diaper, a deodorant composition such as an aerosol, and the like.

Furthermore, since the aforementioned perfume precursor is excellent in storage stability in an aqueous solution system, it may be used for various fabric treating agents for clothing such as a softener and a finishing agent, various cosmetics such as a liquid soap and a lotion, hair cosmetics such as a hair shampoo, a hair rinse, a hair conditioner, and a hair styling agent, various detergents such as a detergent for tableware, a detergent for clothing, and a body detergent, a perfumery, a cologne, a water-based deodorant, a liquid bath additive, and the like.

It is to be noted that though the perfume composition of the present invention is one containing the aforementioned perfume precursor, the perfume precursor is preferably one produced by the aforementioned production method.

[Fabric Treating Agent, Cosmetic, Hair Cosmetic, and Detergent]

The fabric treating agent, cosmetic, hair cosmetic, and detergent of the present invention are those containing the perfume composition of the present invention and are those which sustainedly release the perfume having a phenol structure or a hydroxy-4-pyrane structure. In consequence, when blended in a water-based product, excellent storage stability is revealed.

The content of the perfume precursor in the fabric treating agent of the present invention is preferably 0.001% by mass or more, more preferably 0.01% by mass or more, and still more preferably 0.03% by mass or more; and preferably 10% by mass or less, more preferably 5% by mass or less, and still more preferably 1% by mass or less. The fabric treating agent of the present invention is especially useful in an application for fabric treating agent, such as a detergent for clothing, a softener, etc.

From the viewpoint of effectively utilizing the perfuming method of the present invention which enables the fragrance to be revealed over a long period of time, the perfume composition of the present invention is especially useful in a softener. From the viewpoint of making the hydrolysis of the perfume precursor in the product easy to be inhibited, a softener substrate which is used for the softener is preferably an ester amine obtained through a reaction of a long-chain fatty acid and an alkanolamine and/or a compound obtained through quaternization of such an ester amine by a known method, and more preferably a compound obtained through quaternization of an ester amine that is a reaction product of a plant fatty acid and a trialkanolamine, with dimethyl sulfate.

The content of the perfume precursor in the softener is preferably 0.001% by mass or more, more preferably 0.01% by mass or more, and still more preferably 0.03% by mass or more; and preferably 10% by mass or less, more preferably 5% by mass or less, and still more preferably 1% by mass or less.

The content of the perfume precursor each of the cosmetic and the hair cosmetic of the present invention is preferably 0.001% by mass or more, more preferably 0.01% by mass or more, and still more preferably 0.03% by mass or more; and preferably 10% by mass or less, more preferably 5% by mass or less, and still more preferably 1% by mass or less.

The content of the perfume precursor in the detergent of the present invention, particularly the detergent for clothing is preferably 0.001% by mass or more, more preferably 0.01% by mass or more, and still more preferably 0.03% by mass or more; and preferably 10% by mass or less, more preferably 5% by mass or less, and still more preferably 1% by mass or less.

The content of the perfume precursor in a human body detergent of the present invention is preferably 0.001% by mass or more, more preferably 0.01% by mass or more, and still more preferably 0.03% by mass or more; and preferably 10% by mass or less, more preferably 5% by mass or less, and still more preferably 1% by mass or less.

[Perfuming Method]

The perfuming method of the present invention is a perfuming method including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact with moisture in the air to perform hydrolysis, thereby releasing a perfume.

The perfume precursor is an ester of a perfume having a phenol structure or a hydroxy-4-pyrone structure and an aliphatic monocarboxylic acid or an aliphatic dicarboxylic acid having a relatively long-chain hydrocarbon moiety, and hence, when brought into contact with air, the ester moiety derived from the phenol structure or hydroxy-4-pyrone structure having a hydroxyl group with a relatively high acidity is liable to be relatively hydrolyzed with moisture in the air, so that a fragrance may be revealed over a long period of time. When maltol, ethyl maltol, vanillin, ethyl vanillin, or raspberry ketone is combined as the perfume having a phenol structure or a hydroxy-4-pyrone structure with an aliphatic monocarboxylic acid having 8 or more and 18 or less carbon atoms or an aliphatic dicarboxylic acid having 6 or more and 20 or less carbon atoms, an especially conspicuous effect is brought.

[Use for Perfuming]

The use for perfuming of the present invention is use for perfuming including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact with moisture in the air to perform hydrolysis, thereby releasing a perfume.

Suitable embodiments of the respective components and the like in the use for perfuming of the present invention are those as described above.

In addition to the aforementioned embodiments, the present invention also includes the following embodiments.

<1> A perfuming method including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact with moisture in the air to perform hydrolysis, thereby releasing a perfume.

<2> A perfume composition containing a perfume precursor composed of an ester of a perfume having a phenol structure or a hydroxy-4-pyrone structure and an aliphatic monocarboxylic acid having 8 or more and 18 or less carbon atoms or an aliphatic dicarboxylic acid having 6 or more and 20 or less carbon atoms.

<3> The perfume precursor as set forth in <2>, wherein a pKa of the perfume having a phenol structure or a hydroxy-4-pyrone structure is preferably 13 or less, more preferably 7 or more and 12 or less, and still more preferably 7.5 or more and 11.5 or less.

<4> The perfume precursor as set forth in <2> or <3>, wherein the carbon number of the perfume having a phenol structure is preferably 7 or more, more preferably 8 or more, and still more preferably 9 or more; and preferably 14 or less, more preferably 10 or less, still more preferably 9 or less, and yet still more preferably 9.

<5> The perfume precursor as set forth in any of <2> to <4>, wherein the perfume having a phenol structure is at least one selected from vanillin, ethyl vanillin, isoeugenol, benzyl salicylate, cis-3-hexenyl salicylate, vanillin PGA, cyclohexyl salicylate, eugenol, zingerone, vanitrope, raspberry ketone, methyl salicylate, hexyl salicylate, carvacrol, and thymol.

<6> The perfume precursor as set forth in any of <2> to <5>, wherein the carbon number of the perfume having a hydroxy-4-pyrone structure is preferably 6 or more, and more preferably 7 or more; and preferably 10 or less, more preferably 7 or less, and still more preferably 7.

<7> The perfume precursor as set forth in any of <2> to <6>, wherein the perfume having a hydroxy-4-pyrone structure is maltol or ethyl maltol.

<8> The perfume precursor as set forth in <2>, wherein the perfume is at least one selected from maltol, ethyl maltol, vanillin, ethyl vanillin, and raspberry ketone.

<9> The perfume precursor as set forth in any of <2> to <8>, wherein the perfume is a substance that allows a smell to be sensed, and specifically a fragrance.

<10> The perfume precursor as set forth in any of <2> to <9>, wherein the carbon number of the aliphatic monocarboxylic acid is 8 or more, preferably 10 or more, more preferably 11 or more, and still more preferably 12 or more; and 18 or less, preferably 16 or less, more preferably 14 or less, still more preferably 12 or less, and yet still more preferably 12.

<11> The perfume precursor as set forth in any of <2> to <10>, wherein the aliphatic monocaboxylic acid is preferably at least one selected from enanthic acid, caprylic acid, pelargonic acid, capric acid, undecylic acid, lauric acid, tridecylic acid, myristic acid, pentadecylic acid, palmitic acid, margaric acid, stearic acid, dimethyloctanoic acid, octenoic acid, decenoic acid, dodecenoic acid, tetradecenoic acid, hexadecenoic acid, oleic acid, vaccenic acid, linoleic acid, and linolenic acid; more preferably at least one selected from lauric acid, myristic acid, palmitic acid, stearic acid, and oleic acid; and still more preferably at least one selected from lauric acid, stearic acid, and oleic acid.

<12> The perfume precursor as set forth in any of <2> to <11>, wherein the carbon number of the aliphatic dicarboxylic acid is 6 or more, preferably 8 or more, more preferably 9 or more, and still more preferably 10 or more; and 20 or less, preferably 16 or less, more preferably 14 or less, and still more preferably 12 or less.

<13> The perfume precursor as set forth in any of <2> to <12>, wherein the aliphatic dicarboxylic acid is preferably at least one selected from adipic acid, pimelic acid, suberic acid, azelaic acid, sebacic acid, dodecanedioic acid, and tetradecanedioic acid; more preferably at least one selected from adipic acid, suberic acid, azelaic acid, sebacic acid, and dodecanedioic acid; still more preferably adipic acid or sebacic acid; and yet still more preferably sebacic acid.

<14> A production method of a perfume precursor, wherein a production method of an ester constituting the perfume precursor is any of (i) a method of esterifying directly the aforementioned perfume and the aforementioned aliphatic monocarboxylic acid or aliphatic dicarboxylic acid, thereby producing the perfume precursor; (ii) a method of subjecting an ester obtained by allowing a lower alcohol, such as methanol, etc., and the aforementioned aliphatic monocarboxylic acid or aliphatic dicarboxylic acid to react with each other, to an ester interchange reaction with the aforementioned perfume, thereby producing the perfume precursor; (iii) a method of allowing the aforementioned perfume and an acid halide of the aforementioned aliphatic monocarboxylic acid or aliphatic dicarboxylic acid to react with each other, thereby producing the perfume precursor; and (iv) a method of allowing the aforementioned perfume and an anhydride of the aforementioned aliphatic monocarboxylic acid or aliphatic dicarboxylic acid to react with each other, thereby producing the perfume precursor.

<15> The production method of a perfume precursor as set forth in <14>, wherein a perfume having a phenol structure or a hydroxy-4-pyrone structure and an acid halide of an aliphatic monocarboxylic acid having 8 or more and 18 or less carbon atoms or an acid halide of an aliphatic dicarboxylic acid having 6 or more and 20 or less carbon atoms are subjected to a condensation reaction.

<16> The production method of a perfume precursor as set forth in <14> or <15>, wherein the acid halide of the aliphatic monocarboxylic acid or the acid halide of the aliphatic dicarboxylic acid is one obtained through a reaction of the aliphatic monocarboxylic acid or aliphatic dicarboxylic acid with a halogenating reagent of every kind, such as thionyl chloride, phosphorus trichloride, phosphorus pentachloride, phosphorus tribromide, etc.

<17> The production method of a perfume precursor as set forth in <15> or <16>, wherein the charge amount of the perfume in performing the condensation reaction is preferably 0.9 moles or more, more preferably 0.95 moles or more, and still more preferably 0.98 moles or more; and preferably 1.1 moles or less, more preferably 1.05 moles or less, and still more preferably 1.02 moles or less per mole of the acid halide of an aliphatic monocarboxylic acid.

<18> The production method of a perfume precursor as set forth in <15> or <16>, wherein the charge amount of the perfume in performing the condensation reaction is preferably 1.8 moles or more, more preferably 1.9 moles or more, and still more preferably 1.95 moles or more; and preferably 2.2 moles or less, more preferably 2.1 moles or less, and still more preferably 2.05 moles or less per mole of the acid halide of an aliphatic dicarboxylic acid.

<19> The production method of a perfume precursor as set forth in any of <15> to <18>, wherein a solvent which is used for the condensation reaction is at least one selected from halogenated hydrocarbons, such as chloroform, dichloromethane, etc., aliphatic esters, such as ethyl acetate, isopropyl acetate, etc., aromatic hydrocarbons, such as benzene, toluene, xylene, ethylbenzene, etc., alicyclic hydrocarbons, such as cyclopentane, cyclohexane, methylcyclohexane, decalin, tetralin, etc., and aliphatic hydrocarbons, such as pentane, hexane, heptane, octane, etc.

<20> The production method of a perfume precursor as set forth in any of <15> to <19>, wherein a reaction temperature of the condensation reaction is a boiling point of each of the perfume and the aliphatic monocarboxylic acid or aliphatic dicarboxylic acid or lower; and specifically, it is preferably −20° C. or higher, more preferably −18° C. or higher, still more preferably −15° C. or higher, and yet still more preferably −12° C. or higher; and preferably 80° C. or lower, and more preferably 65° C. or lower.

<21> The production method of a perfume precursor as set forth in any of <15> to <20>, wherein the condensation reaction may be performed at atmospheric pressure or under reduced pressure; and a specific pressure is preferably 80 kPa or more, more preferably 90 kPa or more, and still more preferably 95 kPa or more; and preferably 101 kPa or less.

<22> The production method of a perfume precursor as set forth in any of <15> to <21>, wherein the condensation reaction is a reaction using a basic substance, and as the basic substance, at least one selected from triethylamine, tributylamine, pyridine, picoline, and diazabicycloundecene (DBU), and preferably triethylamine is used.

<23> The production method of a perfume precursor as set forth in <22>, wherein the use amount of the basic substance is preferably 1 mole or more, more preferably 1.01 moles or more, still more preferably 1.02 moles or more, and yet still more preferably 1.04 moles or more; and preferably 1.2 moles or less, more preferably 1.15 moles or less, still more preferably 1.1 moles or less, and yet still more preferably 1.06 moles or less per mole of the acid halide of an aliphatic monocarboxylic acid.

<24> The production method of a perfume precursor as set forth in <22>, wherein the use amount of the basic substance is preferably 2 moles or more, more preferably 2.01 moles or more, still more preferably 2.02 moles or more, and yet still more preferably 2.04 moles or more; and preferably 2.4 moles or less, more preferably 2.3 moles or less, still more preferably 2.2 moles or less, and yet still more preferably 2.15 moles or less per mole of the acid halide of an aliphatic dicarboxylic acid.

<25> A perfume composition containing the perfume precursor as set forth above in any of <2> to <13>.

<26> The perfume composition as set forth in <25>, wherein the perfume composition is a composition that sustainedly releases the perfume having a phenol structure or a hydroxy-4-pyrone structure through hydrolysis.

<27> The perfume composition as set forth in <25> or <26>, further containing at least one selected from other perfume, an oil, a surfactant, and an organic solvent.

<28> An oil-based deodorant composition, a powder detergent, a solid soap, a bath additive, a sanitary material, e.g., a diaper, etc., or a deodorant composit e.g., an aerosol, etc., containing the perfume composition as set forth above in any of <25> to <27>.

<29> Various fabric treating agents for clothing, such as a softener, a finishing agent, etc., various cosmetics, such as a liquid soap, a lotion, etc., hair cosmetics, such as a hair shampoo, a hair rinse, a hair conditioner, a hair styling agent, etc., various detergents, such as a detergent for tableware, a detergent for clothing, a body detergent, etc., a perfumery, a cologne, a water-based deodorant, or a liquid bath additive, each containing the perfume composition as set forth above in any of <25> to <97>.

<30> A fabric treating agent containing the perfume composition as set forth above in any of <25> to <27>.

<31> The fabric treating agent as set forth in <30>, wherein the content of the perfume precursor is preferably 0.001% by mass or more, more preferably 0.01% by mass or more, and still more preferably 0.03% by mass or more; and preferably 10% by mass or less, more preferably 5% by mass or less, and still more preferably 1% by mass or less.

<32> A softener containing the perfume composition as set forth above in any of <25> to <27>.

<33> The softener as set forth in <32>, wherein a softener substrate is preferably an ester amine obtained through a reaction of a long-chain fatty acid and an alkanolamine and/or a compound obtained through quaternization of such an ester amine by a known method, and more preferably a compound obtained through quaternization of an ester amine that is a reaction product of a plant fatty acid and a trialkanolamine, with dimethyl sulfate.

<34> The softener as set forth in <32> or <33>, wherein the content of the perfume precursor is preferably 0.001% by mass or more, more preferably 0.01% by mass or more, and still more preferably 0.03% by mass or more; and preferably 10% by mass or less, more preferably 5% by mass or less, and still more preferably 1% by mass or less.

<35> A cosmetic containing the perfume composition as set forth above in any of <25> to <27>.

<36> The cosmetic as set forth in <35>, wherein the content of the perfume precursor is preferably 0.001% by mass or more, more preferably 0.01% by mass or more, and still more preferably 0.03% by mass or more; and preferably 10% by mass or less, more preferably 5% by mass or less, and still more preferably 1% by mass or less.

<37> A hair cosmetic containing the perfume composition as set forth above in any of <25> to <27>.

<38> The hair cosmetic as set forth in <37>, wherein the content of the perfume precursor in the hair cosmetic is preferably 0.001% by mass or more, more preferably 0.01% by mass or more, and still more preferably 0.03% by mass or more; and preferably 10% by mass or less, more preferably 5% by mass or less, and still more preferably 1% by mass or less.

<39> A detergent containing the perfume composition as set forth above in any of <25> to <27>.

<40> The detergent as set forth in <39>, wherein the detergent is a detergent for clothing, and the content of the perfume precursor in the detergent for clothing is preferably 0.001% by mass or more, more preferably 0.01% by mass or more, and still more preferably 0.03% by mass or more; and preferably 10% by mass or less, more preferably 5% by mass or less, and still more preferably 1% by mass or less.

<41> The detergent as set forth in <39>, wherein the detergent is a body detergent, and the content of the perfume precursor in a human body detergent is preferably 0.001% by mass or more, more preferably 0.01% by mass or more, and still more preferably 0.03% by mass or more; and preferably 10% by mass or less, more preferably 5% by mass or less, and still more preferably 1% by mass or less.

<42> Use for perfuming including applying a water-based product to a fabric or a human body and drying, the water-based product containing a perfume precursor composed of an ester of at least one perfume selected from maltol, ethyl maltol, vanillin, ethyl vanillin, and raspberry ketone and at least one aliphatic monocarboxylic acid or aliphatic dicarboxylic acid selected from lauric acid, myristic acid, palmitic acid, stearic acid, oleic acid, adipic acid, and sebacic acid; and subsequently bringing the perfume precursor into contact with moisture in the air to perform hydrolysis, thereby releasing a perfume.

EXAMPLES

<Production of Ester>

Examples 1 to 13

Example 1

(Production of Ester of Lauric Acid and Ethyl Vanillin)

A 300-mL four-neck flask was charged with 8.95 g (0.041 moles) of lauroyl chloride and 40 mL of dichloromethane in a nitrogen atmosphere and then cooled to 0° C. Meanwhile, a 100-mL dropping funnel was charged with 6.80 g (0.041 moles) of ethyl vanillin, 4.35 g (0.043 moles) of triethylamine, and 40 mL of dichloromethane. The mixture was dropped from the dropping funnel into the flask over 40 minutes such that the reaction temperature was kept at −5° C. to 0° C. After completion of dropping, the resultant was agitated at room temperature (25° C.) for 2 hours. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine and the resulting solution was dried over sodium sulfate. After removing the solvent under reduced pressure, there was obtained 14.20 g (yield: 99%) of an ester of lauric acid and ethyl vanillin as a pale yellow solid.

The measurement results of NMR and IR are shown below.

NMR ($^1$H, 400 MHz): 0.88 (t, J=7 Hz, 3H), 1.20 to 1.50 (m, 19H), 1.78 (quint., J=7 Hz, 2H), 2.59 (t, J=7 Hz, 2H), 4.13 (t, J=7 Hz, 2H), 7.20 (d, J=8 Hz, 1H), 7.46 (d, J=8 Hz, 2H), 9.93 (s, 1H)

IR (KBr): 2918, 2850, 1763, 1693, 1273, 1115, 742 cm$^{-1}$

Example 2

(Production of Ester of Stearic Acid and Ethyl Vanillin)

A 300-mL four-neck flask was charged with 10.00 g (0.033 moles) of stearoyl chloride and 50 mL of dichloromethane in a nitrogen atmosphere and then cooled to 0° C. Meanwhile, a 100-mL dropping funnel was charged with 5.49 g (0.033 moles) of ethyl vanillin, 3.51 g (0.035 moles) of triethylamine, and 40 mL of dichloromethane. The mixture was dropped from the dropping funnel into the flask over 20 minutes such that the reaction temperature was kept at −10° C. to 0° C. After completion of dropping, the resultant was agitated at room temperature (25° C.) for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried, over sodium sulfate. After removing the solvent under reduced pressure, there was obtained 14.18 g (yield: 99%) of an ester of stearic acid and ethyl vanillin as a pale yellow solid.

The measurement results of NMR and IR are shown below.

NMR ($^1$H, 400 MHz): 0.88 (t, J=7 Hz, 3H), 1.20 to 1.50 (m, 31H), 1.78 (quint., J=7 Hz, 2H), 2.59 (t, J=7 Hz, 2H), 4.13 (q, J=7 Hz, 2H), 7.20 (d, J=8 Hz, 1H), 7.46 (d, J=8 Hz, 2H), 9.93 (s, 1H)

IR (KBr): 2918, 2850, 1763, 1693, 1273, 1115, 742 cm$^{-1}$

Example 3

(Production of Ester of Oleic Acid and Ethyl Vanillin)

A 300-mL four-neck flask was charged with 10.00 g (0.033 moles) of oleoyl chloride and 50 mL of dichloromethane in a nitrogen atmosphere and then cooled to 0° C. Meanwhile, a 100-mL dropping funnel was charged with 5.52 g (0.033 moles) of ethyl vanillin, 3.53 g (0.035 moles) of triethylamine, and 40 mL of dichloromethane. The mixture was dropped from the dropping funnel into the flask over 30 minutes such that the reaction temperature was kept at −10° C. to 0° C. After completion of dropping, the resultant was agitated at room temperature (25° C.) for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 14.23 g (yield: 99%) of an ester of oleic acid and ethyl vanillin as a black oily material.

The measurement results of NMR and IR are shown below.

NMR ($^1$H, 400 MHz): 0.88 (t, J=7 Hz, 3H), 1.20 to 1.50 (m, 23H), 1.78 (quint., J=7 Hz, 2H), 2.02 (m, 4H), 2.59 (t, J=7 Hz, 2H), 4.13 (m, 2H), 5.30 to 5.45 (m, 2H), 7.20 (d, J=8 Hz, 1H), 7.46 (d, j=8 Hz, 2H), 9.93 (s, 1H)

IR (NaCl): 2918, 2850, 1763, 1693, 1273, 1115, 742 cm$^{-1}$

Example 4

(Production of Ester of Lauric Acid and Ethyl Maltol)

A 300-mL four-neck flask was charged with 10.00 g (0.046 moles) of lauroyl chloride and 45 mL of dichloromethane in a nitrogen atmosphere and then cooled to 0° C. Meanwhile, a 100-mL dropping funnel was charged with 6.41 g (0.046 moles) of ethyl maltol, 4.86 g (0.048 moles) of triethylamine, and 45 mL of dichloromethane. The mixture was dropped from the dropping funnel into the flask over 30 minutes such that the reaction temperature was kept at −5° C. to 0° C. After completion of dropping, the resultant was agitated at room temperature (25° C.) for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 14.74 g (yield: 100%) of an ester of lauric acid and ethyl maltol as a pale yellow solid.

The measurement results of NMR and IR are shown below.

NMR ($^1$H, 400 MHz): 0.88 (t, J=7 Hz, 3H), 1.20 to 1.45 (m, 21H), 1.75 (quint., J=7 Hz, 2H), 2.59 (m, 4H), 6.39 (d, J=6 Hz, 1H), 7.69 (d, J=6 Hz, 1H)

IR (KBr): 2923, 2854, 1768, 1658, 1160, 1133, 1106, 825 cm$^{-1}$

Example 5

(Production of Ester of Stearic Acid and Ethyl Maltol)

A 300-mL four-neck flask was charged with 10.00 g (0.033 moles) of stearoyl chloride and 33 mL of dichloromethane in a nitrogen atmosphere and then cooled to 0° C. Meanwhile, a 100-mL dropping funnel was charged with 4.66 g (0.033 moles) of ethyl maltol, 3.51 g (0.035 moles) of triethylamine, and 33 mL of dichloromethane. The mixture was dropped from the dropping funnel into the flask over 20 minutes such that the reaction temperature was kept at −5° C. to 0° C. After completion of dropping, the resultant was agitated at room temperature (25° C.) for 2 hours. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 9.60 g (yield: 72%) of an ester of stearic acid and ethyl maltol as a pale yellow solid.

The measurement results of NMR and IR are shown below.

NMR ($^1$H, 400 MHz): 0.88 (t, j=7 Hz, 3H), 1.20 to 1.50 (m, 33H), 1.75 (quint., J=7 Hz, 2H), 2.45 to 2.65 (m, 4H), 6.39 (d, J=6 Hz, 1H), 7.69 (d, J=6 Hz, 1H)

IR (KBr): 2916, 2849, 1766, 1664, 1633, 1170, 847, 829, 717 cm$^{-1}$

Example 6

(Production of Ester of Oleic Acid and Ethyl Maltol)

A 300-mL four-neck flask was charged with 10.00 g (0.033 moles) of oleoyl chloride and 33 mL of dichloromethane in a nitrogen atmosphere and then cooled to 0° C. Meanwhile, a 100-mL dropping funnel was charged with 4.66 g (0.033 moles) of ethyl maltol, 3.53 g (0.035 moles) of triethylamine, and 33 mL of dichloromethane. The mixture was dropped from the dropping funnel into the flask over 30 minutes such that the reaction temperature was kept at −5° C. to 0° C. After completion of dropping, the resultant was agitated at room temperature (25° C.) for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 13.3 g (yield: 99%) of an ester of oleic acid and ethyl maltol as a brown oily material.

The measurement results of NMR and IR are shown below.

NMR ($^1$H, 400 MHz): 0.88 (t, J=7 Hz, 3H), 1.20 to 1.45 (m, 25H), 1.76 (quint., J=10 Hz, 2H), 2.00 to 2.10 (m, 4H), 2.50 to 2.65 (m, 4H), 6.36 (d, J=6 Hz, 1H), 7.67 (d, J=6 Hz, 1H)

IR (NaCl): 2923, 2854, 1768, 1660, 1160, 825, 723 cm$^{-1}$

Example 7

(Production of Ester of Lauric Acid and Raspberry Ketone)

A 300-mL four-neck flask was charged with 10.00 g (0.046 moles) of lauroyl chloride and 46 mL of dichloromethane in a nitrogen atmosphere and then cooled to 0° C. Meanwhile, a 100-mL dropping funnel was charged with 7.51 g (0.046 moles) of raspberry ketone, 4.86 g (0.048 moles) of triethylamine, and 46 mL of dichloromethane. The mixture was dropped from the dropping funnel into the flask over 20 minutes such that the reaction temperature was kept at −5° C. to 0° C. After completion of dropping, the resultant was agitated at room temperature (25° C.) for 4 hours. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 15.71 g (yield: 99%) of an ester of lauric acid and raspberry ketone as a white solid.

The measurement results of NMR and IR are shown below.

NMR ($^1$H, 400 MHz): 0.88 (t, J=7 Hz, 3H), 1.20 to 1.45 (m, 16H), 1.74 (quint., J=7 Hz, 2H), 2.14 (t, 3H), 2.53 (t, J=7 Hz, 2H), 2.47 (t, J=7 Hz, 2H), 2.88 (t, J=7 Hz, 2H) 6.96 (d, J=7 Hz, 2H), 7.15 (d, J=6 Hz, 2H)

IR (KBr): 2916, 2848, 1747, 1705, 1510, 1211, 1167, 926, 852, 814, 719 cm$^{-1}$

Example 8

(Production of Ester of Stearic Acid and Raspberry Ketone)

A 300-mL four-neck flask was charged with 10.00 g (0.033 moles) of stearoyl chloride and 33 mL of dichloromethane in a nitrogen atmosphere and then cooled to 0° C. Meanwhile, a 100-mL dropping funnel was charged with 5.42 g (0.033 moles) of raspberry ketone, 3.51 g (0.035 moles) of triethylamine, and 33 mL of dichloromethane. The mixture was dropped from the dropping funnel into the flask over 20 minutes such that the reaction temperature was kept at −5° C. to 0° C. After completion of dropping, the resultant was agitated at room temperature (25° C.) for 2 hours. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 13.85 g 97%) of an ester of stearic acid and raspberry ketone as a white solid.

The measurement results of NMR and IR are shown below.

NMR ($^1$H, 400 MHz): 0.88 (t, J=7 Hz, 3H) 1.20 to 1.50 (m, 28H), 1.74 (quint., J=7 Hz, 2H), 2.14 (s, 3H), 2.53 (t, J=7 Hz, 3H), 2.74 (t, J=7 Hz, 2H), 2.88 (t, J=7 Hz, 2H), 6.98 (d, J=8 Hz, 1H), 7.18 (d, J=8 Hz, 2H)

IR (KBr): 2914, 2848, 1769, 1705, 1510, 1471, 1367, 1215, 1167, 1144, 1018, 923, 717 cm$^{-1}$

Example 9

(Production of Ester of Oleic Acid and Raspberry Ketone)

A 300-mL four-neck flask was charged with 10.00 g (0.033 moles) of oleoyl chloride and 33 mL of dichloromethane in a nitrogen atmosphere and then cooled to 0° C. Meanwhile, a 100-mL dropping funnel was charged with 5.42 g (0.033 moles) of raspberry ketone, 3.53 g (0.035 moles) of triethylamine, and 33 mL of dichloromethane. The mixture was dropped from the dropping funnel into the flask over 30 minutes such that the reaction temperature was kept at −5° C. to 0° C. After completion of dropping, the resultant was agitated at room temperature (25° C.) for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 13.3 g (yield: 99%) of an ester of oleic acid and raspberry ketone as a brown oily material.

The measurement results of NMR and IR are shown below.

NMR ($^1$H, 400 MHz): 0.86 (t, J=7 Hz, 3H), 1.20 to 1.45 (m, 22H), 1.72 (quint., J=8 Hz, 2H), 1.90 to 2.10 (m, 4H), 2.12 (s, 3H), 2.52 (t, J=8 Hz, 2H), 2.73 (t, J=7 Hz, 2H), 2.87 (t, J=7 Hz, 2H), 5.29 to 5.38 (m, 2H), 6.96 (d, J=8 Hz, 2H), 7.16 (d, J=8 Hz, 2H)

IR (NaCl): 2924, 2854, 1757, 1716, 1508, 1200, 1165, 1136, 1018, 920, 813, 723 cm$^{-1}$

Example 10

(Production of Ester of Stearic Acid and Vanillin)

A 300-mL four-neck flask was charged with 10.00 g (0.033 moles) of stearoyl chloride and 33 mL of dichloromethane in a nitrogen atmosphere and then cooled to 0° C. Meanwhile, a 100-mL dropping funnel was charged with 5.02 g (0.033 moles) of vanillin, 3.51 g (0.035 moles) of triethylamine, and 20 mL of dichloromethane. The mixture was dropped from the dropping funnel into the flask over 30 minutes such that the reaction temperature was kept at −10° C. to 0° C. After completion of dropping, the resultant was agitated at room temperature (25° C.) for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried, over sodium sulfate. After removing the solvent under reduced pressure, there was obtained 13.54 g (yield: 98%) of an ester of stearic acid and vanillin as a pale yellow solid.

The measurement results of NMR and IR are shown below.

NMR ($^1$H, 400 MHz): 0.86 (t, J=7 Hz, 3H), 1.20 to 1.46 (m, 30H), 1.75 (quint., J=7 Hz, 2H), 2.58 (t, J=8 Hz, 2H), 3.88 (s, 3H), 7.19 (d, J=8 Hz, 1H), 7.46 (d, J=8 Hz, 1H), 7.47 (s, 1H), 9.93 (s, 1H)

IR (KBr): 2914, 2850, 1759, 1682, 1589, 1510, 1473, 1383, 1288, 1267, 1138, 1111, 1028, 922, 885, 841, 783, 713 cm$^{-1}$

Example 11

(Production of Ester of Oleic Acid and Vanillin)

A 300-mL four-neck flask was charged with 10.00 g (0.033 moles) of oleoyl chloride and 33 mL of dichloromethane in a nitrogen atmosphere and then cooled to 0° C. Meanwhile, a 100-mL dropping funnel was charged with 5.06 g (0.033 moles) of vanillin, 3.53 g (0.035 moles) of triethylamine, and 33 mL of dichloromethane. The mixture was dropped from the dropping funnel into the flask over 20 minutes such that the reaction temperature was kept at −10° C. to 0° C. After completion of dropping, the resultant was agitated at room temperature (25° C.) for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained. 13.29 g (yield: 99%) of an ester of oleic acid and vanillin as a black oily material.

The measurement results of NMR and IR are shown below.

NMR ($^1$H, 400 MHz): 0.86 (t, J=7 Hz, 3H), 1.20 to 1.50 (m, 22H), 1.75 (quint., =7 Hz, 2H), 1.90 to 2.10 (m, 4H), 2.58 (t, J=7 Hz, 2H), 3.86 (s, 3H), 5.29 to 5.38 (m, 2H), 7.19 (d, J=8 Hz, 1H), 7.46 (d, J=8 Hz, 1H), 7.47 (s, 1H), 9.93 (s, 1H)

IR (NaCl): 2924, 2854, 1765, 1701, 1601, 1502, 1271, 1146, 1111, 1032, 779, 733 cm$^{-1}$

Example 12

(Production of Ester of Sebacic Acid and Ethyl Vanillin)

A 100-mL three-neck flask was charged with 16.62 g (0.1 moles) of ethyl vanillin, 10.32 g (0.102 moles) of triethylamine, and 42 mL of ethyl acetate in a nitrogen atmosphere and then cooled to 0° C. Meanwhile, a 50-mL dropping funnel was charged with 11.96 g (0.05 moles) of sebacoyl chloride. Then, the sebacoyl chloride was dropped from the dropping funnel into the flask over 40 minutes such that the reaction temperature was kept at −5° C. to 5° C. After completion of dropping, the resultant was agitated at room temperature (25° C.) for 2 hours. Thereafter, 15 mL of a 0.7% by mass sulfuric acid aqueous solution was added into the flask, thereby terminating the reaction. The resulting reaction solution was transferred into a separatory funnel and subjected to layer separation. An oil layer was washed with a saturated brine, and the resulting solution was dried over sodium sulfate. After removing the solvent under reduced pressure, there was obtained 23.11 g (yield: 93%) of an ester of sebacic acid and ethyl vanillin as a pale yellow solid.

The measurement results of NMR and IR are shown below.

NMR ($^1$H, 400 MHz): 1.39 (t, J=7 Hz, 6H), 1.42 to 1.50 (m, 811), 1.78 (quint., J=7 Hz, 4H), 2.58 (t, J=7 Hz, 4H), 4.12 (q, J=7 Hz, 4H), 7.17 (d, J=8 Hz, 2H), 7.42 (d, J=8 Hz, 2H), 7.45 (s, 2H), 9.91 (s, 2H)

IR (KBr) 2978, 2927, 1751, 1697, 1267, 1107, 781 cm$^{-1}$

Example 13

(Production of Ester of Adipic Acid and Ethyl Vanillin)

A 100-mL three-neck flask was charged with 16.62 g (0.1 moles) of ethyl vanillin, 10.32 g (0.102 moles) of triethylamine, and 42 mL of ethyl acetate in a nitrogen atmosphere and then cooled to 0° C. Meanwhile, a 50-mL dropping funnel was charged with 9.15 g (0.05 moles) of adipoyl chloride. Then, the adipoyl chloride was dropped from the dropping funnel into the flask over 30 minutes such that the reaction temperature was kept at −5° C. to 5° C. After completion of dropping, the resultant was agitated at room temperature (25° C.) for 2 hours. Thereafter, a white solid produced by the reaction was removed by means of filtration, and the solvent was removed from a filtrate under reduced pressure, thereby obtaining 21.66 g of a crude product. 3.5 g of the crude product was purified by means of silica gel column chromatography (ethyl acetate/hexane=3/7). After removing the solvent under reduced pressure, there was obtained 0.25 g of an ester of adipic acid and ethyl vanillin as a white solid.

The measurement results of NMR and IR are shown below.

NMR ($^1$H, 400 MHz): 1.39 (t, J=7 Hz, 6H), 1.94 (m, 4H), 2.64 to 2.67 (m, 4H), 4.12 (q, J=7 Hz, 4H), 7.18 (d, J=8 Hz, 2H), 7.42 (d, J=8 Hz, 2H), 7.46 (s, 2H), 9.92 (s, 2H)

IR (KBr): 2989, 2933, 1747, 1695, 1261, 1099, 781 cm$^{-1}$

Comparative Examples 1, 2, 8, and 9

Comparative Example 1

(Production of Ester of Lauric Acid and Geraniol)

A 300-mL four-neck flask was charged with 10.00 g (0.045 moles) of lauroyl chloride and 45 mL of dichloromethane in a nitrogen atmosphere and then cooled to 0° C. Meanwhile, a 100-mL dropping funnel was charged with 7.05 g (0.045 moles) of geraniol (carbon number: 10, pKa: 15.7), 4.86 g (0.048 moles) of triethylamine, and 45 mL of dichloromethane. The mixture was dropped from the dropping funnel into the flask over 40 minutes such that the reaction temperature was kept at −5° C. to 0° C. After completion of dropping, the resultant was agitated at room temperature for 2 hours. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 13.19 g (yield: 86%) of an ester of lauric acid and geraniol as a pale yellow oily material.

The measurement results of NMR and IR are shown below.

NMR ($^1$H, 400 MHz): 0.86 (t, J=7 Hz, 3H), 1.20 to 1.34 (m, 16H), 1.55 to 1.64 (m, 5H), 1.66 (s, 3H), 1.68 (s, 3H), 1.98 to 2.12 (m, 4H), 2.27 (t, J=8 Hz, 2H), 4.56 (d, J=8 Hz, 2H), 5.04 to 5.08 (m, 1H), 5.19 to 5.34 (m, 1H)

IR (KBr): 2924, 2854, 1736, 1456, 1377, 1230, 1163, 957, 721 cm$^{-1}$

Comparative Example 2

(Production of Ester of Lauric Acid and Cis-3-Hexenol)

A 100-mL four-neck flask was charged with 2.19 g (0.010 moles) of lauroyl chloride and 20 mL of dichloromethane in a nitrogen atmosphere and then cooled to 0° C. Meanwhile, a 50-mL dropping funnel was charged with 1.00 g (0.010 moles) of cis-3-hexenol (carbon number: 6, pKa: 15.7), 1.04 g (0.010 moles) of triethylamine, and 10 mL of dichloromethane. The mixture was dropped from the dropping funnel into the flask over 60 minutes such that the reaction temperature was kept at −5° C. to 0° C. After completion of dropping, the resultant was agitated at room temperature for 1 hour. 10 mL of a saturated ammonium chloride aqueous solution was added into the flask, thereby terminating the reaction. 150 mL of diethyl ether was added, a produced white solid was removed by means of filtration, and a filtrate was transferred into a separatory funnel. 100 mL of ion-exchanged water was added into the separatory funnel, and an aqueous layer was extracted three times with 50 mL of diethyl ether. The extracted solutions were gathered and washed with a saturated brine, and the resulting solution was dried over sodium sulfate. After removing the solvent under reduced pressure, there was obtained 2.80 g (yield: 99%) of an ester of lauric acid and cis-3-hexenol as a pale yellow oily material.

The measurement results of NMR and IR are shown below.

NMR ($^1$H, 400 MHz): 0.86 (t, J=7 Hz, 3H), 0.95 (t, J=8 Hz, 3H), 1.20 to 1.34 (m, 18H), 1.55 to 1.66 (m, 2H), 2.04 (quint., J=8 Hz, 2H), 2.27 (t, J=8 Hz, 2H), 2.35 (q, J=7 Hz, 2H), 4.04 (t, J=7 Hz, 2H), 5.24 to 5.34 (m, 1H), 5.44 to 5.54 (m, 1H)

IR (KBr): 2924, 2854, 1738, 1458, 1375, 1230, 1166, 721 cm$^{-1}$

Comparative Example 8

(Production of Ester of Succinic Acid and Ethyl

A 100-mL four-neck flask was charged with 16.62 g (0.1 moles) of ethyl vanillin, 10.32 g (0.102 moles) of triethylamine, and 42 mL of ethyl acetate in a nitrogen atmosphere and then cooled to 0° C. Meanwhile, a 50-mL dropping funnel was charged with 7.75 g (0.05 moles) of succinyl chloride. Then, the succinyl chloride was dropped from the dropping funnel into the flask over 30 minutes such that the reaction temperature was kept at −5° C. to 5° C. After completion of dropping, the resultant was agitated at room temperature (25° C.) for 3 hours. Thereafter, a white solid, produced by the reaction was removed by means of filtration, and the solvent was removed from a filtrate under reduced pressure, thereby obtaining 18.80 g of a crude product. 4.2 g of the crude product was purified by means of silica gel column chromatography (ethyl acetate/hexane=3/7). After removing the solvent under reduced pressure, there was obtained 1.95 g of an ester of succinic acid and ethyl vanillin as a pale yellow solid.

The measurement results of NMR and IR are shown below.

NMR ($^1$H, 400 MHz): 1.38 (t, J=7 Hz, 6H), 3.04 (s, 4H), 4.12 (q, J=7 Hz, 4H), 7.20 (d, J=8 Hz, 2H), 7.42 (d, J=8 Hz, 2H), 7.46 (s, 2H), 9.92 (s, 2H)

IR (KBr) 2991, 2939, 1758, 1699, 1257, 1114, 791 cm$^{-1}$

Comparative Example 9

(Production of Ester of Fumaric Acid and Ethyl Vanillin)

A 100-mL four-neck flask was charged with 16.62 g (0.1 moles) of ethyl vanillin, 10.32 g (0.102 moles) of triethylamine, and 42 mL of ethyl acetate in a nitrogen atmosphere and then cooled to 0° C. Meanwhile, a 50-mL dropping funnel was charged with 7.65 g (0.05 moles) of fumaryl chloride. Then, the fumaryl chloride was dropped from the dropping funnel into the flask over 25 minutes such that the reaction temperature was kept at −7° C. to 5° C. After completion of dropping, the resultant was agitated at room temperature (25° C.) for 2 hours. Thereafter, a white solid produced by the reaction was removed by means of filtration, and the solvent was removed from a filtrate under reduced pressure, thereby obtaining 19.72 g of a crude product. 2.8 g of the crude product was purified by means of silica gel column chromatography (ethyl acetate/hexane=3/

7). After removing the solvent under reduced pressure, there was obtained 0.30 g of an ester of fumaric acid and ethyl vanillin as a pale yellow solid.

The measurement results of NMR and IR are shown below.

NMR ($^1$H, 400 MHz): 1.40 (t, J=7 Hz, 6H), 4.15 (q, J=7 Hz, 4H), 7.25 (s, 2H), 7.28 (d, J=8 Hz, 2H), 7.48 (d, J=8 Hz, 2H), 7.50 (s, 2H), 9.95 (s, 2H)

IR (KBr): 2985, 2938, 2738, 1735, 1697, 1274, 1122, 808 cm$^{-1}$

Test Example

<Production of Fabric Treating Agent>

In a 50-mL screw vial "No. 7" (manufactured by Maruemu Corporation), each of the esters obtained in Examples 1 to 13 and Comparative Examples 1, 2, 8, and 9 and a perfume were charged in amounts of 0.5 parts by mass, respectively as converted into the perfume based on 100 parts by mass of an unperfumed liquid softener A having a composition shown in Table 1, and heated at 50° C. for 5 minutes, followed by cooling. There were thus prepared softener compositions as a fabric treating agent. It is to be noted that examples in which the perfume itself was used are designated as Comparative Examples 3 to 7.

TABLE 1

| Unperfumed liquid softener A[2] | Blending amount (% by mass) |
|---|---|
| Cationic softening substrate[1] | 13 |
| Polyoxyethylene (21) lauryl ether | 3.5 |
| Calcium chloride | 0.3 |
| Proxel BDN | 0.03 |
| Ion-exchanged water | Balance |

[1] A compound obtained through quaternization of an ester amine that is a reaction product of a plant fatty acid and triethanolamine in a molar ratio of 1.65/1, with dimethyl sulfate by a conventional method
[2] Blended such that a pH of the liquid softener is 3.2

<Evaluation of Persistence of Fragrance>

Twenty-four cotton towels were repeatedly cleaned five times with a commercially available weakly alkaline detergent "Attack" (manufactured by Kao Corporation) by using an automatic washing machine "NW-6CY", manufactured by Hitachi, Ltd. in advance, and the excessive chemical was removed by indoor drying (detergent concentration: 0.0667% by mass, 47 L of tap water used, water temperature: 20° C., washing: 10 minutes, water-saving rinsing: two times).

In an electric bucket "N-BK2-A", manufactured by Panasonic Corporation, 5 L of tap water was poured, and the softener composition (one preserved at 40° C. for 2 weeks after the preparation) was then dissolved therein (to prepare a treatment bath) in a proportion of 10 g per 1.0 kg of the clothing. After one minute, the two cotton towels which had been pretreated in the aforementioned method were subjected to a dip treatment for 5 minutes. Thereafter, the resulting two cotton towels were transferred into an electric washing machine "NA-35", manufactured by Panasonic Corporation and subjected to a spin-dry treatment for 3 minutes. After the spin-dry treatment, the resulting towels were allowed to stand for drying in a room at 20° C. one night, and the dried towels were then allowed, to stand in a room at 20° C. for one week.

With respect to the towels immediately after the spin-dry treatment, after elapsing one day, and after elapsing 7 days, the fragrance strength of each perfume was subjected to organoleptic evaluation by four expert panelists according to the following criteria, thereby determining an average value. The results are shown in Tables 2 to 4.

Evaluation Criteria
4: Very strongly smelled
3: Strongly smelled
2: Smelled (recognition threshold value)
1: Slightly smelled (detection threshold value)
0: Not smelled

TABLE 2

| | | Example | | | | | | |
|---|---|---|---|---|---|---|---|---|
| | | 1 | 2 | 3 | 4 | 5 | 6 | 7 |
| Perfume | | EV | EV | EV | EM | EM | EM | RK |
| Aliphatic monocarboxylic acid | | C12 | C18(1) | C18(2) | C12 | C18(1) | C18(2) | C12 |
| Aliphatic dicarboxylic acid | | — | — | — | — | — | — | — |
| Evaluation of | Spin-dried fabric | 2.0 | 1.5 | 1.5 | 2.0 | 1.5 | 1.5 | 1.0 |
| persistence of fragrance | One day after drying | 2.5 | 2.5 | 2.5 | 2.0 | 2.0 | 2.0 | 1.0 |
| (softener-treated fabric) | Seven days after drying | 3.5 | 3.5 | 3.5 | 3.0 | 3.0 | 3.0 | 1.5 |

TABLE 3

| | | Example | | | | | |
|---|---|---|---|---|---|---|---|
| | | 8 | 9 | 10 | 11 | 12 | 13 |
| Perfume | | RK | RK | VA | VA | EV | EV |
| Aliphatic monocarboxylic acid | | C18(1) | C18(2) | C(18) | C18(2) | — | — |
| Aliphatic dicarboxylic acid | | — | — | — | — | C6 | C10 |
| Evaluation of | Spin-dried fabric | 1.0 | 1.0 | 1.5 | 1.5 | 1.5 | 1.5 |
| persistence of fragrance | One day after drying | 1.0 | 1.0 | 2.0 | 2.0 | 1.5 | 2.5 |
| (softener-treated fabric) | Seven days after drying | 1.5 | 1.5 | 2.0 | 2.0 | 1.5 | 2.5 |

TABLE 4

| | | Comparative Example | | | | | | | | |
|---|---|---|---|---|---|---|---|---|---|---|
| | | 1 | 2 | 3 | 4 | 5 | 6 | 7 | 8 | 9 |
| Perfume | | GE | HE | EV | EM | RK | GE | HE | EV | EV |
| Aliphatic monocarboxylic acid | | C12 | C12 | — | — | — | — | — | — | — |
| Aliphatic dicarboxylic acid | | — | — | — | — | — | — | — | C4(1) | C4(2) |
| Evaluation of persistence of fragrance (softener-treated fabric) | Spin-dried fabric | 1.0 | 0.5 | 2.0 | 3.0 | 2.0 | 2.0 | 1.0 | 1.5 | 1.5 |
| | One day after drying | 0.5 | 0.5 | 0.5 | 0.5 | 0.5 | 0.5 | 0.5 | 1.0 | 1.0 |
| | Seven days after drying | 0.5 | 0.5 | 0.5 | 0.5 | 0.5 | 0.0 | 0.5 | 1.0 | 1.0 |

It is to be noted that the abbreviations in Tables 2 to 4 are as follows.
<Aliphatic monocarboxylic acid>
C12: Lauric acid
C18(1): Stearic acid
C18(2): Oleic acid
<Aliphatic Dicarboxylic Acid>
C6: Adipic acid
C10: Sebacic acid
C4(1): Succinic acid
C4(2): Fumaric acid
<Perfume>
EV: Ethyl vanillin
EM: Ethyl maltol
RK: Raspberry ketone
VA: Vanillin
GE: Geraniol
HE: Cis-3-hexenol As is clear from Tables 2 to 4, the perfume composition containing a perfume precursor composed of an ester according to the present invention is excellent in storage stability, particularly stability in a water-based product and is capable of sustainedly releasing a perfume over a long period of time, and hence, it is useful for products, such as a fabric treating composition, a softener, a cosmetic, and a detergent.

The invention claimed is:

1. A perfuming method, comprising:
applying a water-based product that comprises a perfume precursor to a fabric or a human body;
drying the water-based product; and
subsequently bringing the perfume precursor into contact with moisture in the air to perform hydrolysis, thereby releasing a perfume,
wherein the water-based product comprises a perfume precursor comprising an ester of i) at least one perfume selected from the group consisting of maltol, ethyl maltol, ethyl vanillin, and raspberry ketone, and ii) at least one aliphatic monocarboxylic acid or aliphatic dicarboxylic acid selected from the group consisting of lauric acid, myristic acid, palmitic acid, stearic acid, oleic acid, adipic acid, and sebacic acid.

2. The perfuming method according to claim 1, wherein the water-based product is at least one selected member from the group consisting of a fabric treating agent, a softener, a cosmetic, a hair cosmetic, and a detergent.

3. The perfuming method according to claim 1, wherein the water-based product is a softener.

4. The perfuming method according to claim 3, wherein the softener comprises a softener substrate that is a quaternized ester amine comprising units of a plant fatty acid and a trialkanolamine.

5. The perfuming method according to claim 3, wherein a content of the perfume precursor in the softener is 0.001% by mass or more and 10% by mass or less.

6. The perfuming method according to claim 3, wherein a content of the perfume precursor in the softener is 0.01% by mass or more and 5% by mass or less.

7. The perfuming method according to claim 3, wherein a content of the perfume precursor in the softener is 0.03% by mass or more and 1% by mass or less.

8. The perfuming method according to claim 1, wherein said perfume is at least one selected from the group consisting of ethyl maltol, vanillin, ethyl vanillin, and raspberry ketone.

9. The perfuming method according to claim 1, wherein said aliphatic monocarboxylic acid or aliphatic dicarboxylic acid is at least one selected from the group consisting of lauric acid, stearic acid, oleic acid, adipic acid, and sebacic acid.

10. The perfuming method according to claim 1, wherein:
said perfume is at least one selected from the group consisting of ethyl maltol, vanillin, ethyl vanillin, and raspberry ketone; and
said aliphatic monocarboxylic acid or aliphatic dicarboxylic acid is at least one selected from the group consisting of lauric acid, stearic acid, oleic acid, adipic acid, and sebacic acid.

11. The perfuming method according to claim 1, wherein said perfume is at least one selected from the group consisting of ethyl maltol, ethyl vanillin, and raspberry ketone.

12. The perfuming method according to claim 1, wherein said aliphatic monocarboxylic acid or aliphatic dicarboxylic acid is at least one selected from the group consisting of lauric acid, stearic acid, and oleic acid.

13. The perfuming method according to claim 1, wherein:
said perfume is at least one selected from the group consisting of ethyl maltol, ethyl vanillin, and raspberry ketone; and
said aliphatic monocarboxylic acid or aliphatic dicarboxylic acid is at least one selected from the group consisting of lauric acid, stearic acid, and oleic acid.

* * * * *